United States Patent [19]

Pavlin

[11] Patent Number: 4,482,765

[45] Date of Patent: Nov. 13, 1984

[54] PREPARATION OF HYDROXYCITRONELLOL

[75] Inventor: Mark S. Pavlin, Lawrenceville, N.J.

[73] Assignee: Union Camp Corporation, Wayne, N.J.

[21] Appl. No.: 507,475

[22] Filed: Jun. 24, 1983

[51] Int. Cl.$^3$ .................. C07C 29/04; C07C 31/20
[52] U.S. Cl. .................. 568/875; 568/485; 568/496; 568/868
[58] Field of Search .................. 568/852, 899, 875

[56] References Cited

U.S. PATENT DOCUMENTS

| | | | |
|---|---|---|---|
| 3,257,467 | 6/1966 | Kovach | 568/899 |
| 4,012,456 | 3/1977 | Chaplits | 568/899 |
| 4,096,194 | 6/1978 | Moy et al. | 568/899 |
| 4,182,920 | 1/1980 | Giles et al. | 568/899 |
| 4,200,766 | 4/1980 | Hoffmann | 568/875 |
| 4,234,748 | 11/1980 | Frampton et al. | 568/899 |

FOREIGN PATENT DOCUMENTS 973832 10/1964 United Kingdom .............. 568/899

Primary Examiner—J. E. Evans
Attorney, Agent, or Firm—Kane, Dalsimer, Kane, Sullivan and Kurucz

[57] ABSTRACT

An improved process for the preparation of hydroxycitronellol by an addition reaction of water with citronellol. This reaction takes place directly on heating a homogeneous solution of citronellol in a mixture of water and an inert solvent selected from the group consisting of acetone, methyl ethyl ketone, glymes, and tetrahydrofuran. The reaction is catalyzed with a cation exchange resin.

1 Claim, No Drawings

PREPARATION OF HYDROXYCITRONELLOL

BACKGROUND OF THE INVENTION

1. Field of the Invention

The invention relates to an improved process for the preparation of hydroxycitronellol by the addition reaction of water with citronellol.

2. Brief Description of the Prior Art

The U.S. Pat. No. 4,200,766 describes the preparation of hydroxycitronellol by the addition reaction of water with citronellol, in the presence of an alkanol solvent and a cation exchange resin catalyst and is representative of prior art methods.

Prior art methods of hydrating citronellol have not been completely satisfactory. The major problems associated with the prior art processes relate to (1) low conversions (about 60 percent yields) and (2) contamination with by-product ethers. The major by-product of the hydration is citronellyl alkyl ether. This by-product, even in low concentrations, adversely affects the odor of the desired product, hydroxycitronellol and the aldehyde made from it, hydroxycitronellal.

By the method of the present invention, the hydration of citronellol to obtain hydroxycitronellol may be carried out, without the formation of contaminant ethers and in high yield. In a preferred embodiment method of the invention, acetone is employed as the solvent for the citronellol reactant. This preferred method has particular advantages over prior art methods. For example, we have found that acetone is an excellent solvent for water, citronellol, and hydroxycitronellol so it allows one to add additional water (up to about 4 parts to one part citronellol and 2 parts acetone) to the reaction mixture, as the reaction proceeds, without loss of homogeneity. That you can use so much water and so little acetone is surprising and boosts conversion to as much as 72 percent. In addition, one can extract the final product solution with an immiscible, non-polar hydrocarbon such as heptane. Unreacted citronellol is concentrated in the hydrocarbon layer and product hydroxycitronellol is concentrated in the acetone-water layer. In this way a product containing 90% hydroxycitronellol is easily made. Citronellol in the heptane layer is easily recovered and recycled.

SUMMARY OF THE INVENTION

The invention comprises a method of preparing hydroxycitronellol, which comprises; heating a mixture of water and citronellol to a temperature of from 40° C. to 120° C. in the presence of an inert solvent selected from the group consisting of acetone, methyl ethyl ketone, glyme (dimethoxyethane), di-, tri-, or tetraglyme (di-, tri-, or tetraethyleneglycol dimethyl ether) and tetrahydrofuran and a catalytic proportion of an acidic cation exchange resin.

Hydroxycitronellol may be used as a fragrance material and is an important intermediate for the preparation of the highly desired scent hydroxycitronellal.

DETAILED DESCRIPTION OF THE PREFERRED EMBODIMENTS OF THE INVENTION

The invention comprises an improved process for the preparation of hydroxycitronellol (3,7-dimethyloctane-1,7-diol) by an addition reaction of water with citronellol 3,7-dimethyloct-6-en-1-ol) according to the schematic formulae:

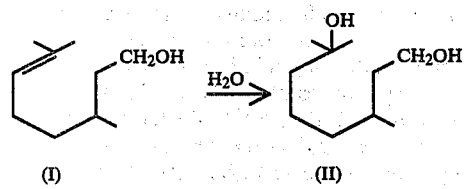

in the presence of a cation exchanger catalyst and a particular solvent which is inert to reaction with the starting reagent (I) and the product (II).

The proportion of reactants, i.e., water and citronellol (I) affects the rate of the reaction. Advantageously from 0.5 to 10 liters of water; preferably 2 to 4 liters are used for each kilogram of citronellol (I). The water is advantageously pre-mixed with the inert solvent to form a homogeneous solution. The ratio of solvent to water is advantageously within the ratio of 1.0:1 to 4.0:1 by volume; preferably 1.0:1 to 2.0:1 by volume at the start of the reaction.

The reaction represented in the above formulae is catalyzed by a catalytic proportion of a strongly acid cation exchange resin. Strongly acid cation exchangers are synthetic resin ion exchangers, i.e. high-polymer three-dimensional networks of carbon chains (matrix) in the form of a gel structure carrying —$SO_3^\ominus$ groups or —$SO_3^\ominus$ and —$O^\ominus$ groups as the charged groups (fixed ions). Essentially, the products concerned are commercial cation exchangers based on polystyrene-sulfonic acid resins or phenolsulfonic acid resins and available, for example, under the following tradenames; Lewatit S 100, Lewatit S 115, Lewatit SP 1080, Lewatit SC 102, Lewatit SPC 118, Amberlite IR 120, Amberlite IR 200, Amberlyst 15, Dowex 50, Permutit RS, Wofatit KPS 200, Duolite C-3, Duolite C-10, Duolite C-25, Wofatit F, Wofatit D, Wofatit P, Zeoxex (Seocarb H), Nalcite HCR, Nalcite HGR, Nalcite HDR, Permutit Q and Permutit RS.

Particularly advantageous results in respect of conversion and reaction time are achieved with cation exchangers having an exceptionally large number of active centers per unit of surface area. Such exchangers include, for example, the particularly finely divided cation exchangers, e.g. Lewatit SPC 108, Lewatit SP 1080 and Lewatit SPC 118 and the coarse-pored ion exchangers, e.g. Amberlyst 15.

The cation exchanger is employed in the commercial hydrated form, but is washed, before use in the reaction, with from about 5 to 10 times its volume of acetone-water mixture.

Further details of the preparation, properties and use of the acid cation exchangers may be found in Ullmanns Encyclopadie der technischen Chemie, 3rd edition, volume 8, 1957, pages 787 et seq., especially pages 806–811 and 814–822.

The proportion of the resin employed as a catalyst in the method of the invention will generally range from 0.1 to 2 kilogram/kilogram of the starting citronellol (I). If the reaction is done batchwise, the product can be recovered simply by decantation and the resin re-used with no loss at all in activity. If the reaction is carried out continuously by passing the aqueous solution of (I) through an exchanger column, it is advantageous to choose conditions corresponding to 1 kg of (I) being passed, per hour, over 5–10 liters of the resin. It is advantageous to wash the exchanger resin before using it for the first time, with the aqueous solution having a composition which roughly corresponds to the water-/acetone ratio in the solutions of (I).

Although the method of the invention may be carried out at temperatures of 40° C. to 120° C., the preferred range is from 50° C. to 80° C. Generally at these temperatures, the reaction is complete in from 10 to 20 hours. Completion of the reaction may be observed by gas chromatographic analysis of the reaction mixture.

When the desired conversion has been reached, the solution is separated from the cation exchanger and is worked up by distillation in the conventional manner to separate the desired hydroxycitronellol (II).

The following examples describe the manner and the process of making and using the invention and set forth the best mode contemplated by the inventor for carrying out the invention.

EXAMPLE 1

A mixture of 100 g Dowex 50W-X8 acidic ion-exchange resin (about 50% water), 50 g citronellol, 100 g acetone, and 50 g water is stirred and heated to reflux (68° C.). Every three hours for 18 hours there is added 25 g additional water. At the end of a total of 20 hours, the mixture is cooled, filtered and analyzed. The molar conversion is 72% and the selectivity, for hydroxycitronellol, 100%. Heptane is shaken (100 ml) with the acetone-water-product mixture for a few minutes and allowed to separate. The ratio of hydroxycitronellol to citronellol in the acetone water layer was 72:28; after extraction, it is 89:11. The hydroxycitronellol is free of contamination with by-product ethers.

EXAMPLE 2

Following the general procedure of Example 1, supra., citronellol (16 parts), Amberlite-IR-120 resin (15 parts), water (30 parts), and solvent (50 parts) were stirred at 78° C. for 15 h. The proportion of products as determined by area percent gas chromatography are given in the Table below, for each solvent used.

TABLE

| Solvent | PRODUCT RATIOS | | |
|---|---|---|---|
| | Hydroxy-citronellol | Citronellol | Citronellol Alkyl Ether |
| Acetone | 59 | 41 | 0 |
| Iso-propanol | 57 | 43 | 1 |
| Tetrahydrofuran | 30 | 70 | 0 |
| Diglyme (diethyleneglycol dimethyl ether) | 59 | 41 | 0 |
| Methanol | 43 | 17 | 40 |
| N—Propanol | 36 | 57 | 7 |

What is claimed:

1. A method of preparing hydroxycitronellol, which comprises; heating a mixture of water and citronellol to a temperature of from 40° C. to 120° C. in the presence of an inert solvent which is acetone, and a proportion of an acidic cation exchange resin.

* * * * *